(12) United States Patent
Gross et al.

(10) Patent No.: US 8,649,863 B2
(45) Date of Patent: Feb. 11, 2014

(54) PACEMAKER WITH NO PRODUCTION

(75) Inventors: Yossi Gross, Moshav Mazor (IL); Amir Dagan, Kibbutz Megiddo (IL); Yotam Reisner, Kiryat Tivon (IL); Offer Glasberg, Zichron Ya'akov (IL); Nitai Hanani, Haifa (IL); Gal Ariav, Givant Ada (IL)

(73) Assignee: Rainbow Medical Ltd., Herzliya (IL)

( * ) Notice: Subject to any disclaimer, the term of this patent is extended or adjusted under 35 U.S.C. 154(b) by 358 days.

(21) Appl. No.: 12/973,484

(22) Filed: Dec. 20, 2010

(65) Prior Publication Data

US 2012/0158081 A1 Jun. 21, 2012

(51) Int. Cl.
*A61N 1/362* (2006.01)

(52) U.S. Cl.
USPC .................................. 607/9; 607/3; 607/70

(58) Field of Classification Search
None
See application file for complete search history.

(56) References Cited

U.S. PATENT DOCUMENTS

| | | | |
|---|---|---|---|
| 3,650,277 A | 3/1972 | Sjostrand et al. | |
| 3,661,148 A | 5/1972 | Kolin | |
| 4,154,227 A | 5/1979 | Krause et al. | |
| 4,201,219 A | 5/1980 | Bozal Gonzalez | |
| 4,474,630 A | 10/1984 | Planck et al. | |
| 4,791,931 A | 12/1988 | Slate | |
| 4,821,723 A | 4/1989 | Baker et al. | |
| 4,938,766 A | 7/1990 | Jarvik | |
| 5,192,271 A | 3/1993 | Kalb et al. | |
| 5,265,011 A | 11/1993 | O'Rourke et al. | |
| 5,265,601 A | 11/1993 | Mehra | |
| 5,324,323 A | 6/1994 | Bui | |
| 5,330,507 A | 7/1994 | Schwartz | |
| 5,372,573 A | 12/1994 | Habib | |
| 5,411,031 A | 5/1995 | Yomtov | |
| 5,423,871 A | 6/1995 | Hoegnelid et al. | |
| 5,458,626 A | 10/1995 | Krause | |
| 5,487,760 A | 1/1996 | Villafana | |
| 5,612,314 A | 3/1997 | Stamler | |
| 5,645,839 A | 7/1997 | Chobanian et al. | |
| 5,649,966 A | 7/1997 | Noren et al. | |
| 5,669,924 A | 9/1997 | Shaknovich | |

(Continued)

FOREIGN PATENT DOCUMENTS

| EP | 0 109 935 | 5/1984 |
|---|---|---|
| EP | 0791341 | 2/1996 |

(Continued)

OTHER PUBLICATIONS

Kis et al., "Repeated Cardiac Pacing Extends the Time During Which Canine Hearts are Protected Against Ischaemia-induced Arrhythmias: Role of Nitric Oxide", J. Molecular Cell Cardiology, 31, 1229-1241, 1999.*

(Continued)

*Primary Examiner* — Kennedy Schaetzle
(74) *Attorney, Agent, or Firm* — Sughrue Mion, PLLC

(57) ABSTRACT

Apparatus and methods are provided for use with a heart of a subject, including a set of one or more electrodes. A control unit paces the heart by driving a first electric current via the electrode set into tissue of the subject, in accordance with a first set of parameters. The control unit stimulates nitric oxide production by a portion of the heart by driving a second electric current via the electrode set into the portion of the heart, in accordance with a second set of parameters. Other embodiments are also described.

23 Claims, 9 Drawing Sheets

(56) References Cited

U.S. PATENT DOCUMENTS

| | | |
|---|---|---|
| 5,707,400 A | 1/1998 | Terry, Jr. et al. |
| 5,762,599 A | 6/1998 | Sohn |
| 5,782,774 A | 7/1998 | Shmulewitz |
| 5,800,464 A | 9/1998 | Kieval et al. |
| 5,800,502 A | 9/1998 | Boutos |
| 5,900,433 A | 5/1999 | Igo et al. |
| 5,904,712 A | 5/1999 | Axelgaard |
| 5,906,641 A | 5/1999 | Thompson |
| 5,913,876 A | 6/1999 | Taylor |
| 5,935,077 A | 8/1999 | Ogle |
| 5,994,444 A | 11/1999 | Trescony et al. |
| 6,023,640 A | 2/2000 | Ross |
| 6,038,485 A | 3/2000 | Axelgaard |
| 6,053,873 A | 4/2000 | Govari |
| 6,058,331 A | 5/2000 | King |
| 6,086,527 A | 7/2000 | Talpade |
| 6,106,477 A | 8/2000 | Miesel et al. |
| 6,120,520 A | 9/2000 | Saadat |
| 6,141,587 A | 10/2000 | Mower et al. |
| 6,200,259 B1 | 3/2001 | March |
| 6,245,103 B1 | 6/2001 | Stinson |
| 6,277,078 B1 | 8/2001 | Porat et al. |
| 6,280,377 B1 | 8/2001 | Talpade |
| 6,347,247 B1 | 2/2002 | Dev |
| 6,411,845 B1 | 6/2002 | Mower et al. |
| 6,445,953 B1 | 9/2002 | Bulkes |
| 6,463,323 B1 | 10/2002 | Conrad-Vlasak |
| 6,485,524 B2 | 11/2002 | Strecker |
| 6,522,926 B1 | 2/2003 | Kieval et al. |
| 6,575,994 B1 | 6/2003 | Marin et al. |
| 6,616,613 B1 | 9/2003 | Goodma et al. |
| 6,616,624 B1 | 9/2003 | Kieval et al. |
| 6,622,041 B2 | 9/2003 | Terry, Jr. et al. |
| 6,632,991 B2 | 10/2003 | Chen |
| 6,647,287 B1 | 11/2003 | Peel, III |
| 6,721,603 B2 | 4/2004 | Zabara et al. |
| 6,810,286 B2 | 10/2004 | Donovan |
| 6,824,561 B2 | 11/2004 | Soykan |
| 6,845,267 B2 | 1/2005 | Harrison |
| 6,850,801 B2 | 2/2005 | Kieval et al. |
| 6,865,416 B2 | 3/2005 | Dev et al. |
| 6,871,092 B2 | 3/2005 | Piccone |
| 6,885,895 B1 | 4/2005 | Whitehurst |
| 6,939,345 B2 | 9/2005 | KenKnight |
| 6,947,792 B2 | 9/2005 | Ben-Haim et al. |
| 6,985,774 B2 | 1/2006 | Kieval et al. |
| 7,044,981 B2 | 5/2006 | Liu et al. |
| 7,062,318 B2 | 6/2006 | Ben-Haim et al. |
| 7,082,336 B2 | 7/2006 | Ransbury et al. |
| 7,090,648 B2 | 8/2006 | Sackner et al. |
| 7,158,832 B2 | 1/2007 | Kieval et al. |
| 7,167,751 B1 | 1/2007 | Whitehurst et al. |
| 7,206,637 B2 | 4/2007 | Salo |
| 7,225,019 B2 | 5/2007 | Jahns et al. |
| 7,229,403 B2 | 6/2007 | Schock |
| 7,269,457 B2 | 9/2007 | Shafer et al. |
| 7,291,113 B2 | 11/2007 | Satoh |
| 7,292,886 B1 | 11/2007 | Kroll |
| 7,299,091 B2 | 11/2007 | Barrett et al. |
| 7,389,149 B2 | 6/2008 | Rossing et al. |
| 7,395,119 B2 | 7/2008 | Hagen et al. |
| 7,452,334 B2 | 11/2008 | Gianchandani |
| 7,476,200 B2 | 1/2009 | Tal |
| 7,486,991 B2 | 2/2009 | Libbus et al. |
| 7,623,926 B2 | 11/2009 | Rossing et al. |
| 7,706,884 B2 | 4/2010 | Libbus |
| 7,706,886 B2 | 4/2010 | Morimoto et al. |
| 7,747,302 B2 | 6/2010 | Milledge |
| 7,765,000 B2 | 7/2010 | Zhang et al. |
| 7,811,221 B2 | 10/2010 | Gross |
| 2001/0044434 A1 | 11/2001 | Lee et al. |
| 2002/0016615 A1 | 2/2002 | Dev |
| 2002/0026228 A1 | 2/2002 | Schauerte |
| 2002/0032468 A1 | 3/2002 | Hill |
| 2002/0077554 A1 | 6/2002 | Schwartz |
| 2002/0103454 A1 | 8/2002 | Sackner |
| 2002/0169413 A1 | 11/2002 | Keren |
| 2003/0036773 A1 | 2/2003 | Whitehurst |
| 2003/0050683 A1 | 3/2003 | Boutos |
| 2003/0060858 A1 | 3/2003 | Kieval et al. |
| 2003/0130715 A1 | 7/2003 | Boutos |
| 2003/0199806 A1 | 10/2003 | Kieval |
| 2003/0204206 A1 | 10/2003 | Padua |
| 2004/0010303 A1 | 1/2004 | Bolea et al. |
| 2004/0019364 A1 | 1/2004 | Kieval et al. |
| 2004/0039417 A1 | 2/2004 | Soykan |
| 2004/0044393 A1 | 3/2004 | Yarden |
| 2004/0054384 A1 | 3/2004 | Nachum |
| 2004/0064090 A1 | 4/2004 | Keren |
| 2004/0106954 A1 | 6/2004 | Whitehurst et al. |
| 2004/0106976 A1 | 6/2004 | Bailey et al. |
| 2004/0133240 A1 | 7/2004 | Adams |
| 2004/0162590 A1 | 8/2004 | Whitehurst et al. |
| 2004/0193092 A1 | 9/2004 | Deal |
| 2004/0254616 A1 | 12/2004 | Rossing et al. |
| 2005/0027346 A1 | 2/2005 | Arkusz et al. |
| 2005/0033407 A1 | 2/2005 | Weber et al. |
| 2005/0090867 A1 | 4/2005 | Lapanashvili |
| 2005/0096710 A1 | 5/2005 | Kieval et al. |
| 2005/0143785 A1 | 6/2005 | Libbus |
| 2005/0149130 A1 | 7/2005 | Libbus |
| 2005/0149132 A1 | 7/2005 | Libbus |
| 2005/0149155 A1 | 7/2005 | Scheiner et al. |
| 2005/0154418 A1 | 7/2005 | Kieval et al. |
| 2005/0203610 A1 | 9/2005 | Tzeng |
| 2005/0209652 A1 | 9/2005 | Whitehurst et al. |
| 2005/0232965 A1 | 10/2005 | Falotico |
| 2005/0233962 A1 | 10/2005 | Lue et al. |
| 2005/0240229 A1 | 10/2005 | Whitehurst et al. |
| 2005/0251212 A1 | 11/2005 | Kieval et al. |
| 2006/0004417 A1 | 1/2006 | Rossing et al. |
| 2006/0004420 A1 | 1/2006 | Rossing et al. |
| 2006/0004430 A1 | 1/2006 | Rossing et al. |
| 2006/0074453 A1 | 4/2006 | Kieval et al. |
| 2006/0100668 A1 | 5/2006 | Ben-David et al. |
| 2006/0111626 A1 | 5/2006 | Rossing et al. |
| 2006/0149124 A1 | 7/2006 | Forsell |
| 2006/0149345 A1 | 7/2006 | Boggs et al. |
| 2006/0167540 A1 | 7/2006 | Masters et al. |
| 2006/0173507 A1 | 8/2006 | Mrva et al. |
| 2006/0217588 A1 | 9/2006 | Gross et al. |
| 2006/0217772 A1 | 9/2006 | Libbus et al. |
| 2006/0229677 A1 | 10/2006 | Moffitt et al. |
| 2006/0259085 A1 | 11/2006 | Zhang et al. |
| 2006/0265038 A1 | 11/2006 | Hagen et al. |
| 2006/0276844 A1 | 12/2006 | Alon |
| 2006/0293712 A1 | 12/2006 | Kieval et al. |
| 2007/0021673 A1 | 1/2007 | Arbel et al. |
| 2007/0021786 A1 | 1/2007 | Parnis et al. |
| 2007/0021790 A1 | 1/2007 | Kieval et al. |
| 2007/0021792 A1 | 1/2007 | Kieval et al. |
| 2007/0021794 A1 | 1/2007 | Kieval et al. |
| 2007/0021796 A1 | 1/2007 | Kieval et al. |
| 2007/0021797 A1 | 1/2007 | Kieval |
| 2007/0021798 A1 | 1/2007 | Kieval et al. |
| 2007/0021799 A1 | 1/2007 | Kieval et al. |
| 2007/0027496 A1 | 2/2007 | Parnis et al. |
| 2007/0038255 A1 | 2/2007 | Kieval et al. |
| 2007/0038259 A1 | 2/2007 | Kieval et al. |
| 2007/0038260 A1 | 2/2007 | Kieval et al. |
| 2007/0038261 A1 | 2/2007 | Kieval et al. |
| 2007/0038262 A1 | 2/2007 | Kieval et al. |
| 2007/0049989 A1 | 3/2007 | Rossing et al. |
| 2007/0060972 A1 | 3/2007 | Kieval et al. |
| 2007/0106340 A1 | 5/2007 | Bolea et al. |
| 2007/0142879 A1 | 6/2007 | Greenberg et al. |
| 2007/0150009 A1 | 6/2007 | Kveen et al. |
| 2007/0156179 A1 | 7/2007 | S.E. |
| 2007/0156198 A1 | 7/2007 | Rossing et al. |
| 2007/0156201 A1 | 7/2007 | Rossing et al. |
| 2007/0167984 A1 | 7/2007 | Kieval et al. |
| 2007/0185542 A1 | 8/2007 | Bolea et al. |
| 2007/0185543 A1 | 8/2007 | Rossing et al. |
| 2007/0196428 A1 | 8/2007 | Glauser et al. |

(56) References Cited

U.S. PATENT DOCUMENTS

| | | | |
|---|---|---|---|
| 2007/0198064 A1 | 8/2007 | Lapanashvili et al. | |
| 2007/0248676 A1 | 10/2007 | Stamler et al. | |
| 2007/0248850 A1 | 10/2007 | Heller | |
| 2007/0276270 A1 | 11/2007 | Tran | |
| 2007/0276442 A1 | 11/2007 | Hagen et al. | |
| 2007/0276459 A1 | 11/2007 | Rossing et al. | |
| 2007/0282385 A1 | 12/2007 | Rossing et al. | |
| 2007/0293927 A1 | 12/2007 | Frank et al. | |
| 2008/0004673 A1 | 1/2008 | Rossing et al. | |
| 2008/0009916 A1 | 1/2008 | Rossing et al. | |
| 2008/0009917 A1 | 1/2008 | Rossing et al. | |
| 2008/0021336 A1 | 1/2008 | Dobak | |
| 2008/0046016 A1 | 2/2008 | Ben-David et al. | |
| 2008/0046054 A1 | 2/2008 | Hjelle et al. | |
| 2008/0051767 A1 | 2/2008 | Rossing et al. | |
| 2008/0058872 A1 | 3/2008 | Brockway et al. | |
| 2008/0071363 A1 | 3/2008 | Tuval et al. | |
| 2008/0082137 A1 | 4/2008 | Kieval et al. | |
| 2008/0097540 A1 | 4/2008 | Bolea et al. | |
| 2008/0119898 A1 | 5/2008 | Ben-David | |
| 2008/0119911 A1 | 5/2008 | Rosero | |
| 2008/0132972 A1 | 6/2008 | Shuros et al. | |
| 2008/0140167 A1 | 6/2008 | Hagen et al. | |
| 2008/0154349 A1 | 6/2008 | Rossing et al. | |
| 2008/0161865 A1 | 7/2008 | Hagen | |
| 2008/0161887 A1 | 7/2008 | Hagen | |
| 2008/0167690 A1 | 7/2008 | Cody et al. | |
| 2008/0167693 A1 | 7/2008 | Kieval et al. | |
| 2008/0167694 A1 | 7/2008 | Bolea et al. | |
| 2008/0167696 A1 | 7/2008 | Cates et al. | |
| 2008/0167699 A1 | 7/2008 | Kieval et al. | |
| 2008/0171923 A1 | 7/2008 | Bolea et al. | |
| 2008/0172101 A1 | 7/2008 | Bolea et al. | |
| 2008/0172104 A1 | 7/2008 | Kieval et al. | |
| 2008/0177364 A1 | 7/2008 | Bolea et al. | |
| 2008/0195174 A1 | 8/2008 | Walker et al. | |
| 2008/0215117 A1 | 9/2008 | Gross et al. | |
| 2009/0005845 A1* | 1/2009 | David et al. | 607/122 |
| 2009/0036975 A1 | 2/2009 | Ward | |
| 2009/0062874 A1 | 3/2009 | Teacey et al. | |
| 2009/0198097 A1 | 8/2009 | Gross | |
| 2009/0198308 A1 | 8/2009 | Gross | |
| 2009/0204170 A1 | 8/2009 | Hastings | |
| 2009/0228078 A1 | 9/2009 | Zhang et al. | |
| 2010/0010556 A1 | 1/2010 | Zhao et al. | |
| 2010/0076247 A1 | 3/2010 | Zilbershlag et al. | |
| 2010/0094373 A1 | 4/2010 | Sharma | |
| 2010/0211131 A1 | 8/2010 | Williams et al. | |
| 2010/0305392 A1 | 12/2010 | Gross et al. | |

FOREIGN PATENT DOCUMENTS

| | | |
|---|---|---|
| WO | 99/26530 | 6/1999 |
| WO | WO 00/02501 | 1/2000 |
| WO | WO 02/26314 | 4/2002 |
| WO | WO 03/076008 | 9/2003 |
| WO | WO 03/082080 | 10/2003 |
| WO | WO 03/082403 | 10/2003 |
| WO | WO 2004/014456 | 1/2004 |
| WO | WO 2004/073484 | 9/2004 |
| WO | 2005/065771 A1 | 7/2005 |
| WO | WO 2005/084389 | 9/2005 |
| WO | WO 2005/097256 | 10/2005 |
| WO | WO 2006/012033 | 2/2006 |
| WO | WO 2006/012050 | 2/2006 |
| WO | WO 2006/032902 | 3/2006 |
| WO | WO 2006/041664 | 4/2006 |
| WO | WO 2006/064503 | 6/2006 |
| WO | 2006/098928 | 9/2006 |
| WO | WO 2006/094273 | 9/2006 |
| WO | WO 2006/123346 | 11/2006 |
| WO | WO 2006/125163 | 11/2006 |
| WO | WO 2007/013065 | 2/2007 |
| WO | WO 2007/047152 | 4/2007 |
| WO | WO 2007/064895 | 6/2007 |
| WO | WO 2007/106533 | 9/2007 |
| WO | WO 2007/113818 | 10/2007 |
| WO | WO 2007/113833 | 10/2007 |
| WO | WO 2007/114860 | 10/2007 |
| WO | WO 2007/118090 | 10/2007 |
| WO | WO 2007/136850 | 11/2007 |
| WO | WO 2007/136851 | 11/2007 |
| WO | WO 2008/039982 | 4/2008 |
| WO | WO 2008/083120 | 7/2008 |
| WO | WO 2008/083235 | 7/2008 |
| WO | WO 2008/100390 | 8/2008 |
| WO | 2009/017647 | 2/2009 |
| WO | WO 2009/095918 | 8/2009 |
| WO | WO 2009/095920 | 8/2009 |

OTHER PUBLICATIONS

Rubaj et al., "Biventricular versus right ventricular pacing decreases immune activation and augments nitric oxide production in patients with chronic heart failure", European Journal Heart Failure, Oct. 2006; 8(6), Epub Feb. 7, 2006.*

An Office Action dated Oct. 2, 2012, which issued during the prosecution of U.S. Appl. No. 12/851,214.

An Office Action dated Sep. 18, 2012, which issued during the prosecution of U.S. Appl. No. 12/023,896.

An English Translation of an Office Action dated Oct. 8, 2012, which issued during the prosecution of Chinese Patent Application No. 200980111617.8.

A Supplementary European search Report dated Dec. 14, 2012, which issued during the prosecution of European Patent Application No. 06766171.

An International Search Report and a Written Opinion both dated Dec. 19, 2011, which issued during the prosecution of Applicant's PCT/IL11/00636.

An Office Action dated Mar. 13, 2012, which issued during the prosecution of U.S. Appl. No. 12/023,896.

An Office Action dated Mar. 15, 2012, which issued during the prosecution of U.S. Appl. No. 12/792,227.

The unequal influences of the left and right vagi on the control of the heart and pulmonary artery in the rattlesnake, *Crotalus durissus*, by Taylor, The Journal of Experimental Biology 212, 145-151 Aug. 2008.

Coronary vascular sympathetic beta-receptor innervation, by Hamiton, American Journal of Physiology, vol. 230, No. 6, Jun. 1976.

An Office Action dated Aug. 9, 2011, which issued during the prosecution of U.S. Appl. No. 12/023,896.

Sherman AJ, "Blockade of nitric oxide synthesis reduces myocardial oxygen consumption in vivo", Circulation 95:1328-1334, 1997.

Kugiyama K, "Nitric oxide activity is deficient in spasm arteries of patients with coronary spastic angina", Circulation 94:266-272, 1996.

Sabbah H et al., "Global left ventricular remodeling with the Acorn Cardiac Support Device: Hemodynamic and angiographic findings in dogs with heart failure", Heart Failure 10(2): 109-115, 2005. (Only First Page).

"Improving the Thromboresistivity of Chemical Sensors via Nitric Oxide Release: Fabrication and in Vivo Evaluation of NO-Releasing Oxygen-Sensing Catheters," by MH Schoenfisch et al., Anal. Chem., 72 (6), 1119-1126, 2000.

"Endogenous and Exogenous Nitric Oxide Protect Against Intracoronary Thrombosis and Reocclusion After Thrombolysis," by Sheng-Kun Yao et al., Circulation. 1995;92: 1005-1010.

"Improving the biocompatibility of in vivo sensors via nitric oxide release," by Jae Ho Shin et al., Analyst, 2006, 131, 609-615.

Cheetah Medical Inc. manufactures the Cheetah Reliant, Jan. 23, 2008.

CardioMEMS, Inc., manufactures the EndoSure® Wireless AAA Pressure Measurement System, Nov. 11, 2005.

Sulzer IntraTherapeutics Inc. manufactures the IntraCoil® Self-Expanding Peripheral Stent (IntraCoil® Stent), Jun. 28, 2002.

"Comparison of neurogenic contraction and relaxation in *Canine corpus* cavernosum and penile artery and vein", Hayashida, et al. Jpn. J. Pharmacol. 72:231-240 (1996), p. 232 col. 2, para 1; p. 238, col. 2, para 2.

(56) References Cited

OTHER PUBLICATIONS

An International Search Report and a Written Opinion both dated Jul. 13, 2009, which issued during the prosecution of Applicant's PCT/IL09/000117.

An International Search Report and a Written Opinion both dated May 12, 2009, which issued during the prosecution of Applicant's PCT/IL09/000115.

An Office Action dated Nov. 18, 2009, which issued during the prosecution of Applicant's U.S. Appl. No. 12/023,900.

"Vagus nerve stimulation as a method to temporarily slow or arrest the heart," by Matheny, Ann Thorac Surg. Jun. 1997;63(6 Suppl):S28-9—an abstract.

"Heart rate variability," by Task Force of the European Society of Cardiology and the North American Society of Pacing and Electrophysiology, European Heart Journal (1996) 17, 354-381.

"Heart rate and vasomotor control during exercise," by Vallais, Proceedings of the 29th Annual International Conference of the IEEE EMBS, Cité Internationale, Lyon, France, Aug. 23-26, 2007.

"Effects of chronic baroreceptor stimulation on the autonomic cardiovascular regulation in patients with drug-resistant arterial hypertension," by Wustmann, Hypertension 2009;54;530-536.

"Sympathovagal balance is major determinant of short-term blood pressure variability in healthy subjects," by Laitinen, Am J Physiol Heart Circ Physiol 276:1245-1252, 1999.

"Optimal frequency ranges for extracting information on cardiovascular autonomic control from the blood pressure and pulse interval spectrograms in mice," by Baudrie, Am J Physiol Regul Integr Comp Physiol 292: R904-R912, 2007.

"Neural influences on cardiovascular variability: possibilities and pitfalls," by Malpas, Am J Physiol Heart Circ Physiol 282: H6-H20, 2002.

"Vagus nerve stimulation decreases left ventricular contractility in vivo in the human and pig heart," by Lewis, J Physiol. Jul. 15, 2001; 534(Pt 2): 547-552.

An International Preliminary Examination Report on Patentability dated Aug. 12, 2010, which issued during the prosecution of Applicant's PCT/IL09/000117.

An International Preliminary Examination Report on Patentability dated Aug. 12, 2010, which issued during the prosecution of Applicant's PCT/IL09/000115.

"Preparation and characterization of implantable sensors with nitric oxide release coatings," by MC Frost, Microchemical Journal vol. 74 Issue: 3, Jun. 2003 pp. 277-288—selected sections attached.

"Beneficial effects of nitric oxide on cardiac diastolic function: the flip side of the coin," by Paulus WJ, Heart Failure Review 5(4):337-344 (2000).

"Loss of nitric oxide production in the coronary circulation after the development of dilated cardiomyopathy: a specific defect in the neural regulation of coronary blood flow," by Gong Z, Clinical and Experimental Pharmacology and Physiology 23(8): 715-721 (1996)—an abstract.

An Office Action dated Jun. 19, 2012, which issued during the prosecution of U.S. Appl. No. 11/995,904.

An Office Action dated Jul. 18, 2012, which issued during the prosecution of U.S. Appl. No. 13/210,778.

An Office Action dated Aug. 29, 2012, which issued during the prosecution of U.S. Appl. No. 12/792,227.

An Office Action dated Aug. 1, 2012, which issued during the prosecution of U.S. Appl. No. 12/957,799.

\* cited by examiner

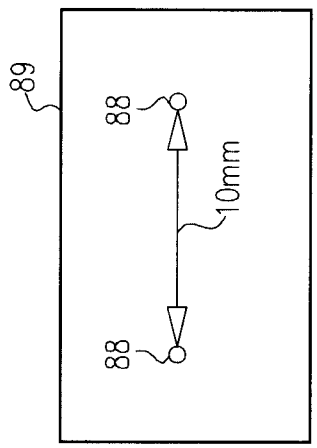
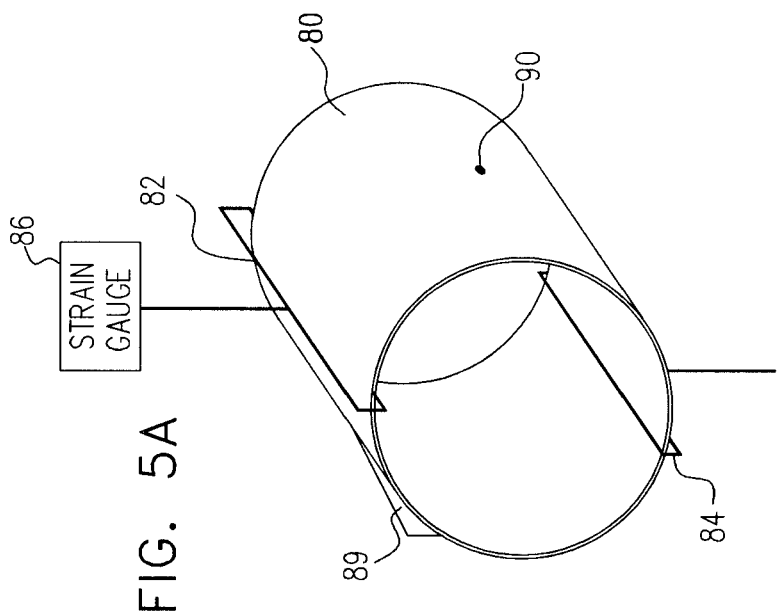

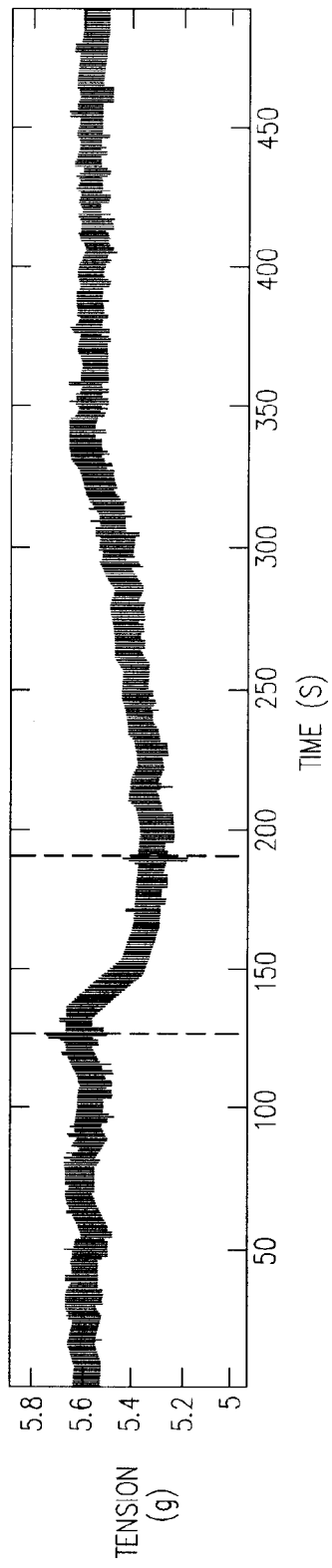
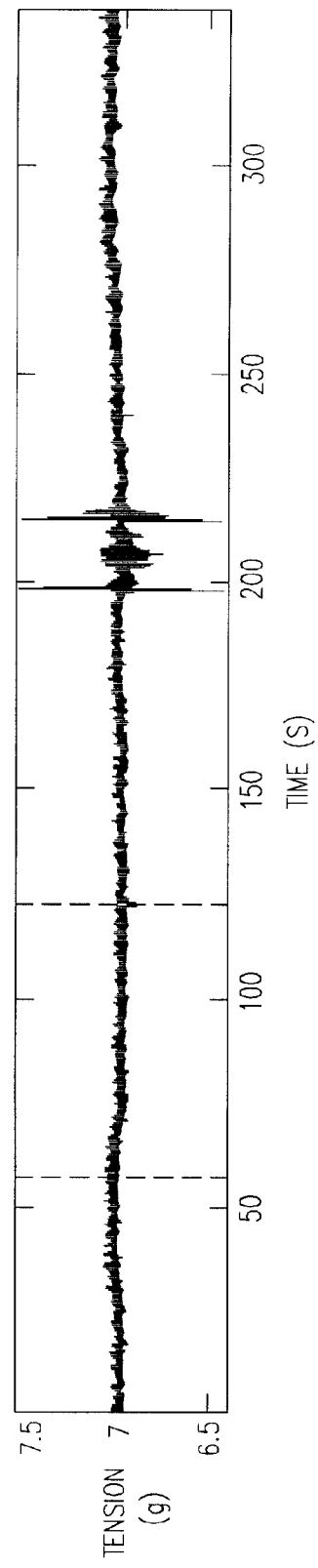

PACEMAKER WITH NO PRODUCTION

FIELD OF EMBODIMENTS OF THE INVENTION

Some applications of the present invention generally relate to medical apparatus. Specifically, some applications of the present invention relate to implantable medical apparatus for enhancing cardiac function.

BACKGROUND

Cardiac arrhythmias are disorders of the beating of the heart, whereby the electrical activity of the heart is irregular, faster, or slower than normal. Some arrhythmias are minor and can occur in an otherwise asymptomatic heart, whereas some arrhythmias may indicate a serious problem and lead to heart disease, stroke or sudden death.

SUMMARY OF EMBODIMENTS

For some applications of the present invention, a set of one or more electrodes are surgically implanted into the heart of a subject. A control unit is configured to drive the electrodes to drive a current into a portion of the heart of the subject to stimulate nitric oxide (NO) production. Typically, the enhanced NO production dilates coronary blood vessels, thereby increasing coronary perfusion.

For some applications, the control unit comprises a cardiac pacemaker control unit. Typically, the control unit is configured to drive a first electric current via the set of one or more electrodes into atrial or ventricular tissue of the subject to pace the heart. The control unit is also configured to drive a second electric current via the set of one or more electrodes into a portion of the heart to stimulate nitric oxide production. For some applications, the control unit is configured to drive the first and second electric currents via at least one common electrode in the set of electrodes. Alternatively, the control unit is configured to drive the second current into a portion of the heart via electrodes in the set of electrodes that are different from those electrodes that are used to pace the heart.

For some applications, the control unit is a component of an implantable cardioverter defibrillator (ICD).

Alternatively or additionally, the control unit is configured to apply the first electric current in a biventricular pacing mode, e.g., as part of cardiac resynchronization therapy for treating heart failure.

For some applications, an ischemic site of the heart is identified, and at least some of the electrodes are placed at the ischemic site, or at an arterial site upstream of the ischemic site. The control unit drives these electrodes to apply the NO stimulating current, thereby enhancing perfusion of the ischemic site. As appropriate for a given application, the ischemia-relieving nitric oxide enhancement may be performed acutely (e.g., within the first hours or days following myocardial infarction), or in a chronic manner. Electrical cardiac ischemia relief as described may be performed in combination with or in the absence of cardiac pacing.

It is hypothesized by the inventors that application of the pulse pattern that induces NO production also increases the mechanical compliance of cardiac muscle tissue. Some applications of the present invention include identifying patients with heart failure (e.g., diastolic heart failure), and applying the signal to enhance NO production in order to increase mechanical compliance of cardiac muscle tissue and thereby treat the heart failure.

It is also hypothesized by the inventors that the production of nitric oxide as described herein exercises the cardiac muscle itself, and over weeks, months, and longer, strengthens the cardiac muscle.

For some applications, the control unit does not pace the heart. Typically, the electrodes are coupled to an outer surface of the heart during a transthoracic implantation procedure.

For some applications, the electrical stimulation described herein is provided in combination with nitroglycerin therapy, or other pharmaceutical therapy. The inventors hypothesize that such a combined electrical/pharmaceutical therapy allows for lower doses of the nitroglycerin to be administered, thereby reducing side effects of the nitroglycerin while maintaining the same clinical benefits.

There is therefore provided, in accordance with some applications of the present invention, apparatus for use with a heart of a subject, including:
    a set of one or more electrodes; and
    a control unit, configured to:
        pace the heart by driving a first electric current via the electrode set into tissue of the subject, in accordance with a first set of parameters, and
        stimulate nitric oxide production by a portion of the heart by driving a second electric current via the electrode set into the portion of the heart, in accordance with a second set of parameters.

For some applications, the control unit is configured to drive the first and second electric currents into a sinoatrial node of the subject.

For some applications, the control unit is configured to drive the first and second electric currents into an atrioventricular node of the subject.

For some applications, the control unit is configured to drive the first and second electric currents into a Purkinje fiber of the subject.

For some applications, the apparatus further includes a sensor configured to sense a level of activity of the subject and to generate a signal in response thereto, and the control unit is configured to receive the signal and to stimulate the nitric oxide production in response to the signal.

For some applications, the apparatus further includes a sensor configured to sense a level of activity of the subject and to generate a signal in response thereto, and the control unit is configured to:
    set a parameter of the first electric current in response to the signal, and
    designate a frequency parameter of the second electric current independently of the signal.

For some applications, the control unit is configured to stimulate the nitric oxide production by driving the second electric current during an excitable period of the heart.

For some applications, the control unit is configured to stimulate the nitric oxide production by driving the second electric current during a refractory period of the heart.

For some applications, the control unit is configured to stimulate the nitric oxide production by driving the second electric current during an excitatory period and a refractory period of the heart.

For some applications, the control unit is configured to stimulate the nitric oxide production by driving the second electric current independently of any sensed level of activity of the subject.

For some applications,
    the set of electrodes includes at least a first and a second electrode, the control unit is configured to pace the heart by driving the first electric current via the first electrode into the tissue of the subject, and the control unit is configured to stimulate the nitric oxide production by driving the second electric current via the second electrode into the portion of the heart.

For some applications, the control unit is configured to enhance coronary perfusion by stimulating the nitric oxide production.

For some applications, the control unit is configured to stimulate the nitric oxide production independently of the cardiac cycle.

For some applications, the control unit is configured to stimulate the nitric oxide production substantially without causing action potentials in the portion of the heart.

For some applications, the control unit is configured to pace the heart and to stimulate the nitric oxide production by driving the first and second electric currents via a same one of the electrodes in the set of electrodes.

For some applications, the control unit is configured to pace the heart and to stimulate the nitric oxide production by driving the first and second electric currents via respective electrodes in the set of electrodes.

For some applications, the control unit is configured to stimulate the nitric oxide production by driving the second electric current in each of 24 hours in a day.

For some applications, the control unit is configured to stimulate the nitric oxide production by the portion of the heart by configuring the second electric current to have an amplitude below the excitation level of the heart of the subject.

For some applications, the control unit is configured to initiate driving of the second current less than 5 ms after terminating the first current.

For some applications, the control unit is configured to wait at least 5 ms after terminating the first current before initiating the second current.

For some applications, the control unit is configured to stimulate the nitric oxide production by the portion of the heart by driving the second electric current with a frequency of more than 20 Hz.

For some applications, the control unit is configured to stimulate the nitric oxide production by the portion of the heart by driving the second electric current for between 20% and 50% of each cardiac cycle.

For some applications, the control unit is configured to stimulate the nitric oxide production in accordance with a duty cycle.

For some applications, the control unit is configured to drive the second current during fewer than 10% of the minutes in a given day.

For some applications, the control unit is configured to drive the second current during between 10% and 30% of the minutes in a given day.

For some applications, the apparatus further includes a detector configured to detect a cardiac cycle of the subject and to generate a signal in response thereto, and the control unit is configured to receive the signal and, in response thereto, to drive the second current in coordination with the cardiac cycle of the subject.

For some applications, the control unit is configured to stimulate the nitric oxide production during diastole.

For some applications, the control unit is configured to detect an ECG signal of the subject and to initiate driving of the second current in response to detecting an R-wave of the subject's ECG signal.

For some applications, the control unit is configured to drive the second current within 50 ms prior to diastole.

For some applications, the control unit is configured to drive the second current between 10 ms and 20 ms prior to diastole.

For some applications, the control unit is configured to pace the heart by driving the first electric current with an amplitude of 1-4 mA.

For some applications, the control unit is configured to pace the heart by configuring the first electric current to have an amplitude of 1.5-3 mA.

For some applications, the control unit is configured to stimulate the nitric oxide production by the portion of the heart by configuring the second electric current to have an amplitude of 15-35 mA.

For some applications, the control unit is configured to stimulate the nitric oxide production by the portion of the heart by configuring the second electric current to have an amplitude of 25-33 mA.

For some applications, the control unit is configured to stimulate the nitric oxide production by driving the second current as a train of pulses into the portion of the heart.

For some applications, the control unit is configured to stimulate the nitric oxide production by driving the second electric current as a train of monophasic pulses.

For some applications, the control unit is configured to stimulate the nitric oxide production by driving the second electric current as a train of biphasic pulses.

For some applications, the control unit is configured to configure each pulse to have a pulse width of 1-5 ms.

There is additionally provided, in accordance with some applications of the present invention, a method for treating a heart of a subject, including:

pacing the heart by driving a first electric current into tissue of the heart, in accordance with a first set of parameters; and stimulating nitric oxide production by a portion of the heart by driving a second electric current into the portion of the heart, in accordance with a second set of parameters.

There is further provided, in accordance with some applications of the present invention, apparatus for use with a heart of a subject, including:

a set of one or more electrodes configured to be implanted into an outer surface of the heart; and a control unit, configured to stimulate nitric oxide production by a portion of the heart by driving the electrodes to drive an electric current into the outer surface of the heart.

For some applications, the control unit is configured to stimulate the nitric oxide production by driving the electric current during an excitatory period of the heart.

For some applications, the control unit is configured to stimulate the nitric oxide production by driving the electric current during a refractory period of the heart.

For some applications, the control unit is configured to stimulate the nitric oxide production by driving the electric current during an excitatory period and a refractory period of the heart.

For some applications, at least one of the electrodes includes a screw electrode.

For some applications, the control unit is configured to stimulate the nitric oxide production by the portion of the heart by driving the electric current for between 20% and 50% of each cardiac cycle.

For some applications, the control unit is configured to stimulate the nitric oxide production by driving the electric current as a train of pulses into the portion of the heart.

For some applications, the control unit is configured to stimulate the nitric oxide production by driving the electric current as a train of monophasic pulses.

For some applications, the control unit is configured to stimulate the nitric oxide production by driving the electric current as a train of biphasic pulses.

For some applications, the control unit is configured to configure each pulse to have a pulse width of 1 ms to 5 ms.

For some applications, the apparatus further includes a mesh supporting the set of electrodes, and configured to be implanted around the outer surface of the heart.

For some applications, the mesh is configured to inhibit remodeling of the heart by applying a compressive force to the heart.

For some applications, the mesh is configured to apply a force to the heart that is insufficient to inhibit remodeling of the heart.

There is additionally provided, in accordance with some applications of the present invention, a method for treating a heart of a subject, including:

implanting a set of one or more electrodes into an outer surface of the heart; and stimulating nitric oxide production by a portion of the heart by driving an electric current into the outer surface of the heart via the electrodes.

There is further provided, in accordance with some applications of the present invention, a method for treating a heart of a subject, including:

identifying the subject as having diastolic heart failure; and in response to the identifying, treating the diastolic heart failure by stimulating nitric oxide production by a portion of the heart, by driving an electric current into the portion of the heart.

There is additionally provided, in accordance with some applications of the present invention, a method for treating a heart of a subject, including:

identifying the subject as having ischemic cardiac tissue; and in response to the identifying, treating the ischemic cardiac tissue by stimulating nitric oxide production by a portion of the heart that vascularizes the ischemic cardiac tissue, by driving an electric current into the portion of the heart.

There is further provided, in accordance with some applications of the present invention, a method for treating a heart of a subject, including:

identifying the subject as having reduced coronary artery perfusion;

administering to the subject a dosage of a pharmaceutical that increases the coronary artery perfusion, the dosage being less than a dosage that is standard for increasing the coronary artery perfusion based on physical characteristics of the subject, assuming that the subject is not also treated in an invasive manner; and increasing the coronary artery perfusion by stimulating nitric oxide production by a portion of the heart, by driving an electric current into the portion of the heart.

The present invention will be more fully understood from the following detailed description of embodiments thereof, taken together with the drawings, in which:

BRIEF DESCRIPTION OF THE DRAWINGS

FIGS. 5A-B are schematic illustrations of a set-up of an experiment that was conducted in accordance with an application of the present invention;

FIGS. 8A-D are graphs showing the tension measured in an aortic ring in response to electrical stimulation (FIG. 8A-B), and in response to the administration of substance P neuropeptide (FIGS. 8C-D).

DETAILED DESCRIPTION OF EMBODIMENTS

Figure 1:
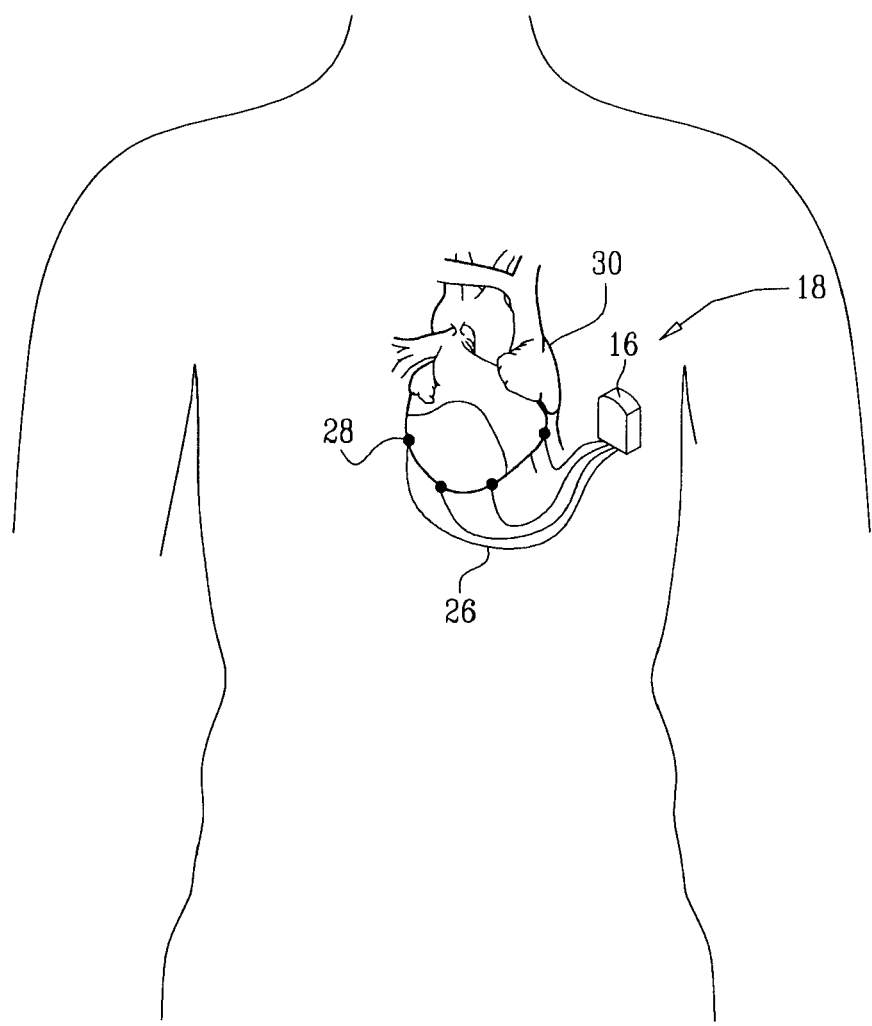
FIG. 1 is a schematic illustration of a control unit, and electrodes implanted into the outer surface of the heart, in accordance with some applications of the present invention.

Reference is now made to FIG. 1, which is a schematic illustration of a system 18 comprising a control unit 16 and a set of one or more electrodes 28 implanted into the outer surface of the heart 30 of a subject, in accordance with some applications of the present invention. Control unit 16 is coupled to electrodes 28 via electrical leads 26, and is configured to drive electrodes 28 to drive an electric current into the heart. Alternatively, control unit 16 drives the electrodes wirelessly (for example, from outside the subject's body). Control unit 16 is configured to enhance coronary perfusion by stimulating nitric oxide production by a portion of the heart of the subject, by driving the current via electrodes 28 into a portion of the heart of the subject.

For some applications, at least one of electrodes 28 is a screw electrode. Alternatively or additionally, electrodes 28 are supported on a mesh that is implanted around the outer surface of the heart. For some applications, the mesh holds the electrodes in place, without applying substantial forces to the heart (e.g., forces which would prevent remodeling of the heart). Alternatively, the mesh constrains the heart and prevents remodeling of the heart, for example, using the Acorn Cardiac Support Device described in "Global left ventricular remodeling with the Acorn Cardiac Support Device: Hemodynamic and angiographic findings in dogs with heart failure," by Sabbah H et al., Heart Failure Reviews 10(2):109-115 (2005), which is incorporated herein by reference.

For some applications, control unit 16 transmits a signal for driving the electrodes via a transmitter (e.g., a transmitting coil) that is placed inside a vein or an artery of the subject in the vicinity of the subject's heart. For example, the control unit may be implanted inside the subject's body, and/or outside the subject's body, and wiredly coupled to the transmitter. The transmitter may be placed in the subject's vena cava, pulmonary vein, and/or pulmonary artery, and a signal may be driven via the transmitter to an antenna disposed on the outside of the subject's heart and that is in electrical communication with electrodes 28. For example, the antenna may be disposed on the mesh described hereinabove.

For some applications, the electrodes act as the antenna. Typically, the transmitter is placed inside the vein or the artery such that it is at a distance from electrodes 28 of more than 5 mm and/or less than 20 mm, e.g., 5-20 mm. Typically, placement of the transmitter in the vein or the artery facilitates transmission of the signal from the control unit to the electrodes, due to the proximity of the vein or the artery to the electrodes. Further typically, the dimensions of the vein or the artery in which the transmitter is placed are such that the vein is able to accommodate a transmitting coil, even in the absence of a rigid housing for housing the coil.

Figure 2:
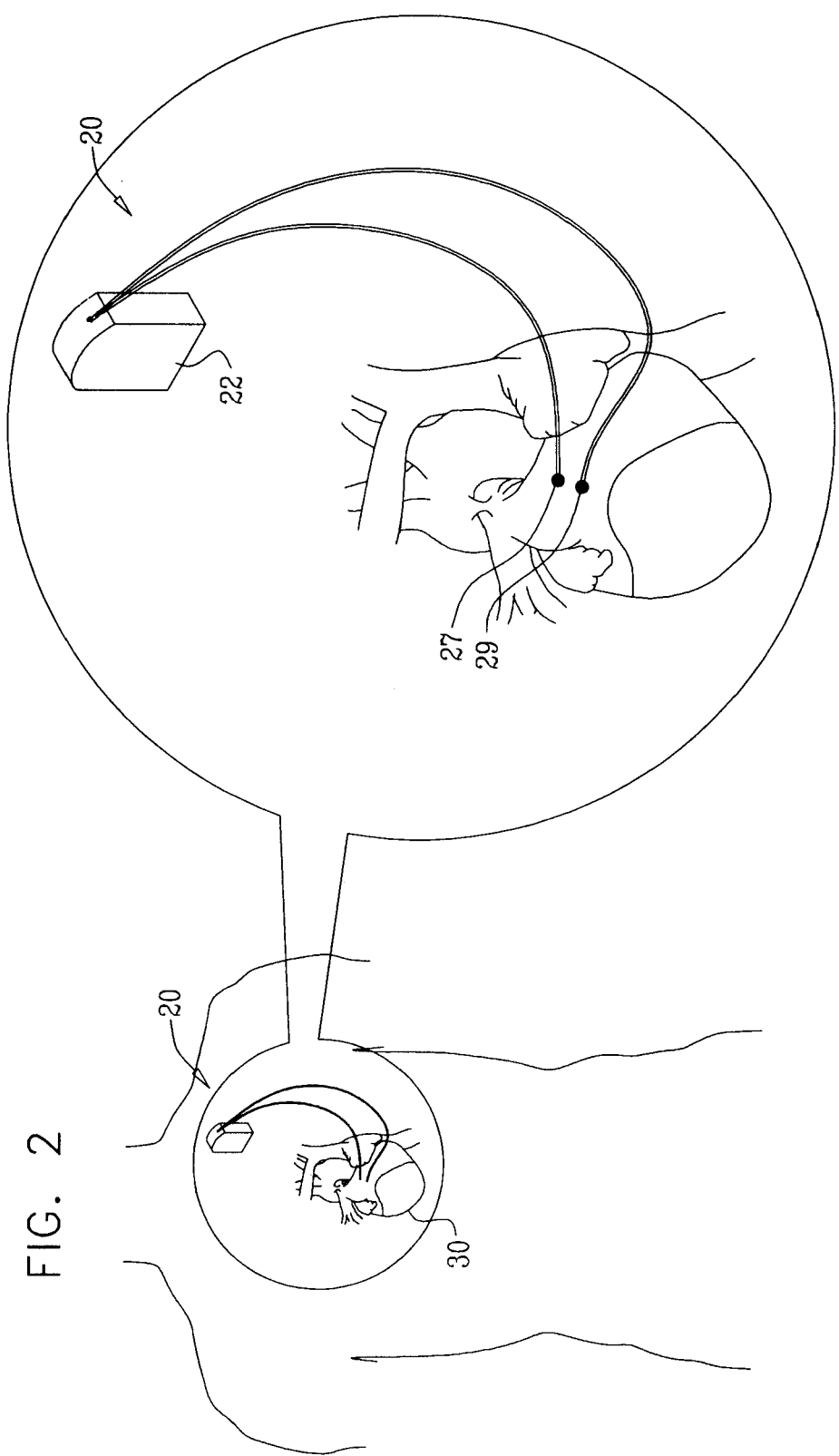
FIG. 2 is a schematic illustration of a pacemaker implanted in the heart of the subject, in accordance with another application of the present invention.

Reference is now made to FIG. 2, which is a schematic illustration of a pacemaker 20 implanted into the heart of the subject, in accordance with some applications of the invention. Pacemaker 20 comprises a control unit 22 coupled to a set of one or more electrodes, e.g., an electrode 27 and/or an electrode 29. For some applications, system 18, described with respect to FIG. 1, includes pacemaker 20, and control unit 16, described with respect to FIG. 1, includes control unit 22. Control unit 22 drives the electrode set to drive an electric current into the heart. Control unit 22 paces the heart by driving a first electric current via electrode 27 into tissue of the heart. Control unit 22 also enhances coronary perfusion by stimulating nitric oxide production by a portion of the heart by driving a second electric current via the electrode set into a portion of the heart of the subject. For some applications, control unit 22 paces the heart and stimulates the nitric oxide production by driving the first and second electric currents via the same one of the electrodes in the set of electrodes (i.e., electrode 27). Alternatively, control unit 22 paces the heart by driving the first electric current via one of the electrodes in the set of electrodes (i.e., electrode 27), and stimulates the nitric oxide production by driving the second electric current into another electrode from the set of electrodes (i.e., electrode 29).

For some applications, control unit 22 drives the second electrical current into the portion of heart 30 in coordination with the cardiac cycle of the subject. For example, the control unit may include a sensor configured to sense the subject's cardiac cycle, and to generate a cardiac-cycle signal in response thereto. The control unit drives the second current in response to the cardiac-cycle signal. For some applications, control unit 22 stimulates the nitric oxide production by driving the second electric current into the portion of the heart at the initiation of the T-wave of an ECG, or within 50 ms prior to diastole (for example, 10 ms to 20 ms prior to diastole). For some applications, control unit 22 stimulates the nitric oxide production by driving the second electric current into the portion of the heart during diastole. For some applications control unit 22 drives the second electric current during the excitable period of the heart. In other applications, control unit stimulates nitric oxide production by driving the second electric current into the portion of the heart during the refractory period. In an alternative application, control unit 22 stimulates nitric oxide production by driving the second electric current into the portion of the heart during both the excitatory period and the refractory period. For some applications, control unit 22 drives the second electrical current into the portion of heart 30 independently of the cardiac cycle of the subject.

For some applications, a sensor coupled to control unit 22 is configured to sense a physiological parameter of the subject and to generate a signal in response thereto. Control unit 22 is configured to receive the signal and in response thereto, drive the second current into the portion of heart 30. For example, the sensor may comprise a motion sensor, configured to sense the level of activity of the subject, such that control unit 22 is configured to receive the signal and in response thereto, increase coronary artery dilation by driving the second current, in accordance with the level of activity of the subject. Thus, for these applications, in response to activity that stresses heart 30 and may cause angina, control unit 22 enhances coronary artery dilation by enhancing nitric oxide production.

For some applications, the second current is driven in response to the detection of the R-wave of the subject's ECG signal. For example, the current may be driven for a time period of more than 200 ms, and/or less than 300 ms (e.g., 200-300 ms) from the onset of the subject's R-wave.

Alternatively, control unit 22 drives the second electrical current into the portion of heart 30 independently of any sensed physiological parameter of the subject, either (a) for its entire period of operation within the patient, or (b) for periods of time that are greater than, for example, one hour. For some applications, control unit 22 is configured to stimulate nitric oxide production by driving a current generally continuously into a portion of the heart, i.e., in each of 24 hours in a day. In other applications, control unit 22 is configured to stimulate nitric oxide production by driving the second current in accordance with a duty cycle, e.g., by applying the second current in accordance with a duty cycle that prescribes current application during fewer than 10% of the minutes in a given day, or during between 10%-30% of the minutes in a given day. For some applications, control unit 22 (a) paces the heart by driving the first electric current into tissue of the heart, in response to the sensed physiological parameter of the subject, and (b) drives the second electrical current into tissue of the heart independently of any sensed physiological parameter of the subject.

For some applications, control unit 22 drives the second electrical current into the portion of heart 30, substantially without causing action potentials in that particular portion of the heart.

For some applications, control unit 22 drives the first and the second electric currents into a sinoatrial node of the subject. In other applications, control unit 22 drives the first and the second electric currents into an atrioventricular node of the subject. In an alternative application, control unit 22 drives the first and the second electric currents into the Purkinje fibers of the subject.

Figure 3:
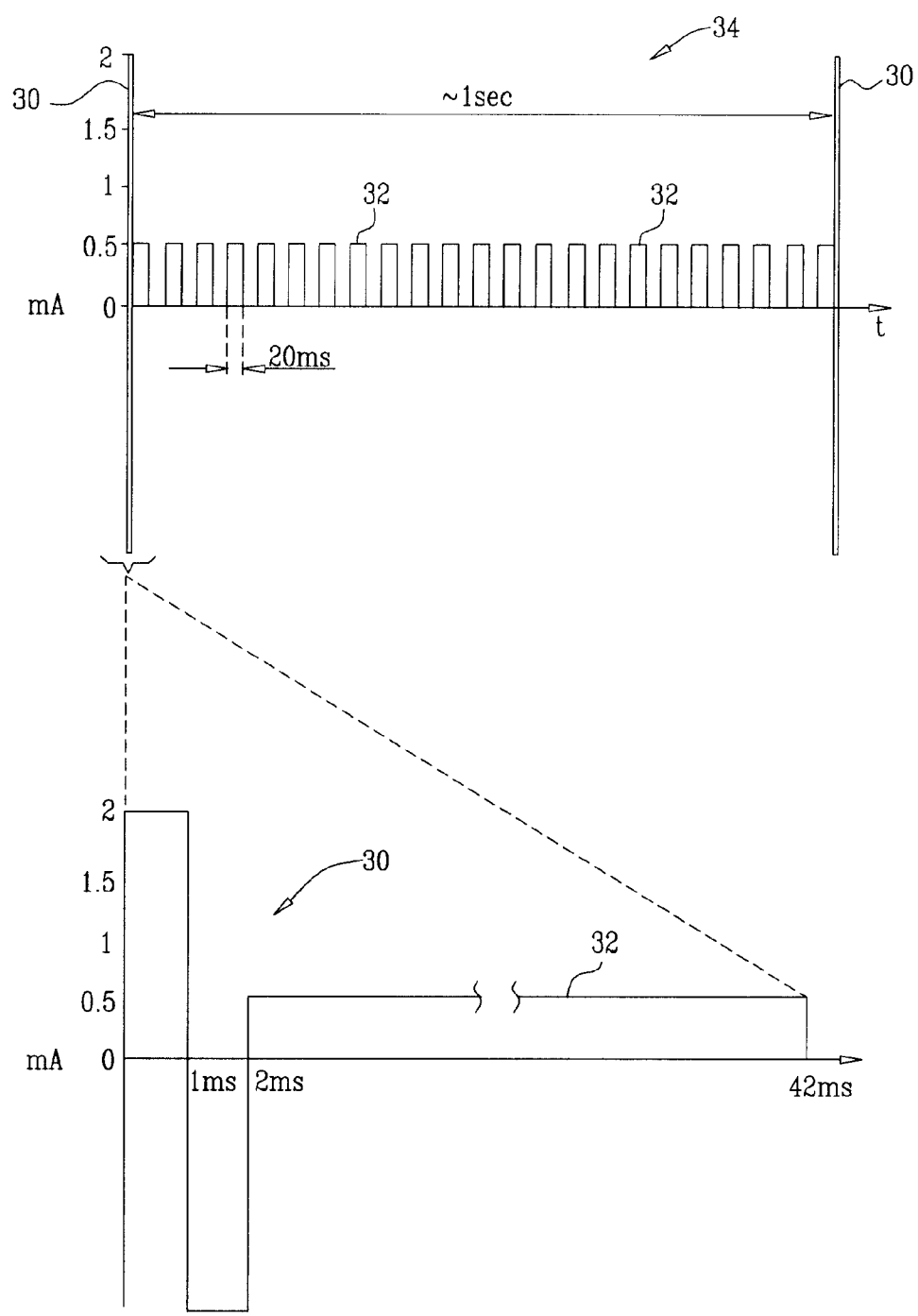
FIGS. 3 and 4 are graphs showing a compound signal for stimulating the heart, in accordance with some applications of the present invention.
Figure 4:
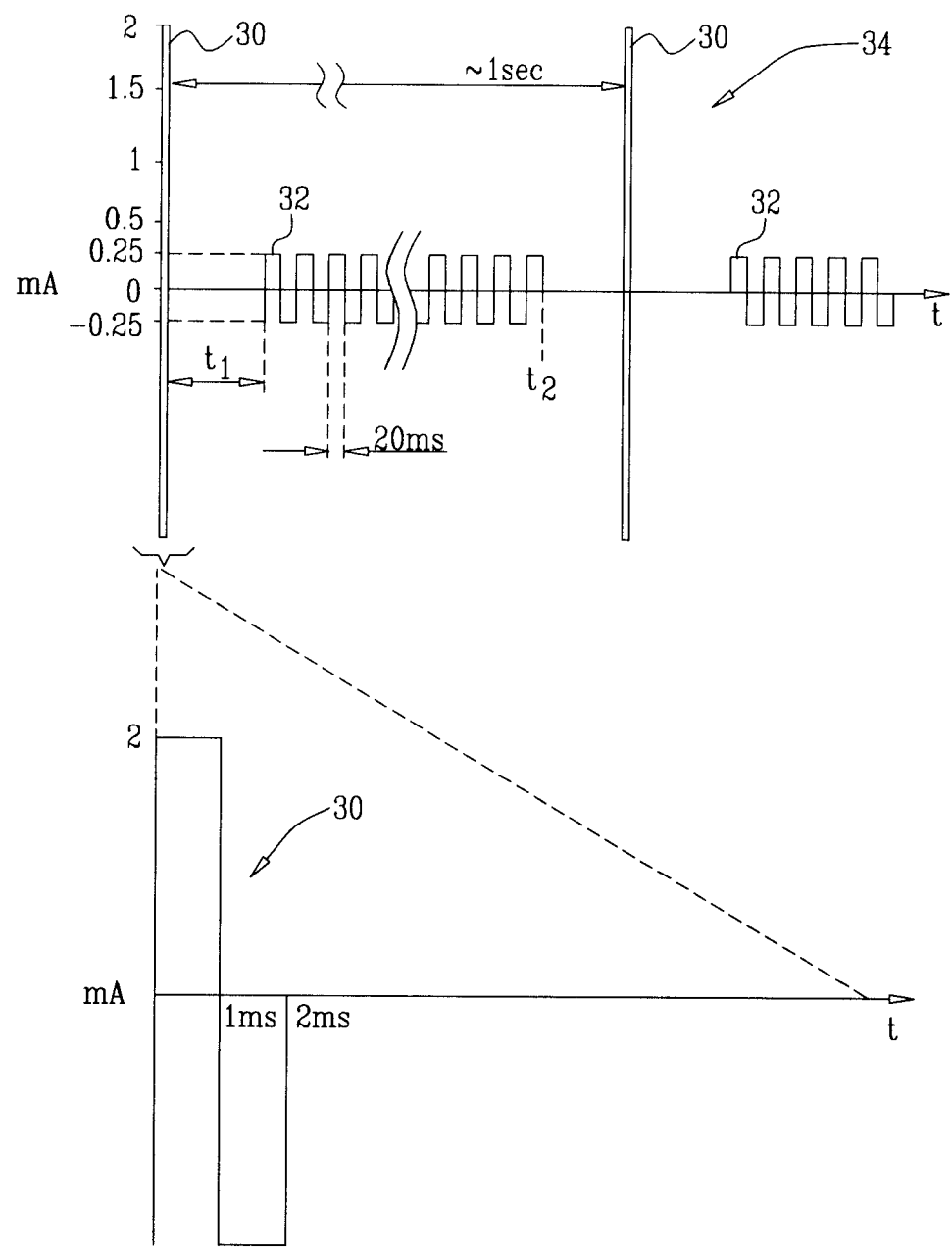

Reference is now made to FIGS. 3 and 4, which are two graphs illustrating a compound signal 34, applied to heart 30 in accordance with some applications of the present invention. Compound signal 34 comprises two sub-signals: sub-signal 30, which paces heart 30; and sub-signal 32, which stimulates nitric oxide production in the portion of heart 30.

For some applications, sub-signal 32 is applied to the portion of heart 30 for substantially the entire cardiac cycle, as shown in FIG. 3. Alternatively, sub-signal 32 is applied for a smaller portion of each cardiac cycle, for example by being applied during between 20% and 50% of each cardiac cycle (it being appreciated that values above or below this range may be suitable for various patients based on their medical condition and/or the amount of nitric oxide which it is desired to generate).

It is noted that the purpose of FIGS. 3 and 4 is to illustrate how sub-signals 30 and 32 may be combined into a compound signal, and that, although sub-signals 30 and 32 are shown in FIGS. 3 and 4 having specific parameters (e.g., specific frequencies and amplitudes), the parameters that are shown are not necessarily used for the sub-signals. Typically, the parameters of sub-signal are in accordance with the parameters provided hereinbelow with reference to FIGS. 7A-C.

For some applications, sub-signal 32 is applied as a train of monophasic pulses (FIG. 3) or biphasic pulses (FIG. 4). Although sub-signal 32 is shown in FIG. 3 as having equally-spaced pulses (e.g., 20 ms on, 20 ms off), some applications utilize an off period following each pulse that is longer or shorter than the duration of each pulse (typically between 50% and 200% of the duration of the applied pulse).

For some applications, control unit 22 applies sub-signal 30 and then waits for t1 ms prior to initiating sub-signal 32. For example, the control unit may wait at least 5 ms before initiating sub-signal 32. Or, the control unit may wait less than 5 ms before initiating sub-signal 32. Control unit 22 terminates application of sub-signal 32 at time t2.

Control unit 22 paces the heart of the subject by driving sub-signal 30 with a frequency that is between 0.8 Hz and 2 Hz, typically approximately 1 Hz, into tissue of the heart. Control unit 22 paces the heart of the subject by driving sub-signal 30 with an amplitude of 1-4 mA, e.g., 1.5-3 mA. The control unit typically stimulates the nitric oxide production by configuring sub-signal 32 to have an amplitude below the excitation level of the heart.

Reference is now made to FIGS. 5A-B, which are schematic illustrations of apparatus that was used in an experiment that was conducted in accordance with an application of the present invention. A 15 mm ring 80 of an aorta was dissected from a pig, and was held in place using upper and lower support elements 82 and 84. Upper support element 82 was connected to a strain gauge 86, such that the strain gauge measured the tension in the aortic ring. Two unipolar epicardial electrodes (Medtronic CapSure Epi 4965) were placed on the adventitia of the aortic ring on one side of the aortic ring (i.e., ipsilaterally to each other, with respect to the aortic ring). The ipsilateral electrodes were coupled to one another by a custom made support 89 (shown in FIG. 5B), at a longitudinal distance of 10 mm from one another. Another electrode 90 was placed on the adventitia of the aortic ring on the side of the aortic ring contralateral to the side on which electrodes 88 were placed.

Aortic ring 80 was electrically stimulated during respective time periods by (a) driving a current into the aortic ring via the two ipsilateral electrodes 88, and (b) driving a current into the aortic ring via one of electrodes 88 and contralateral electrode 90. The current was driven at an amplitude of 15 mA, with a frequency of 50 Hz, and with a pulse width of 4 ms. The tension in the aortic ring before, during, and after stimulation of the aortic ring by the electrodes was measured.

Figure 6A:
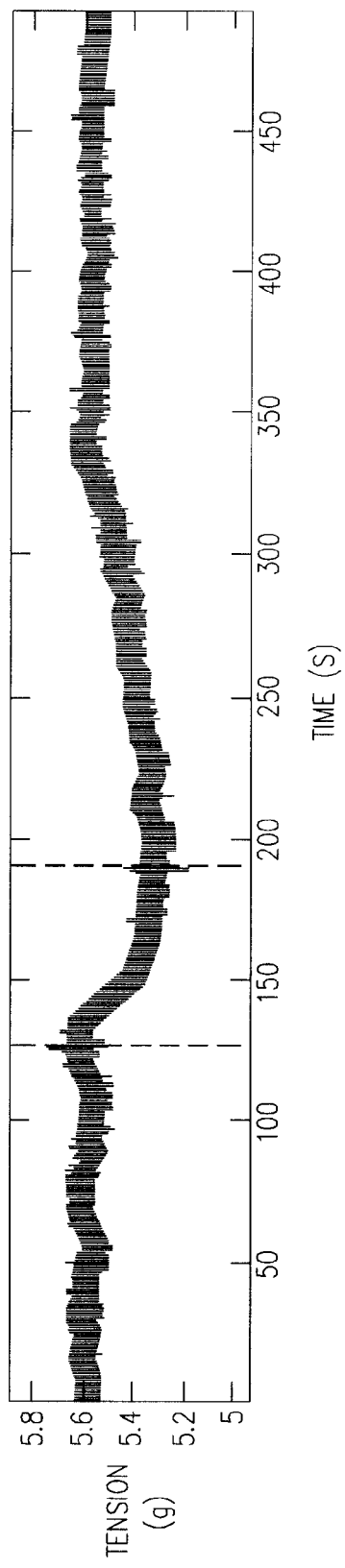
FIGS. 6A-B are graphs showing the tension that was measured in an aortic ring before, during and after stimulation of the ring by, respectively, two ipsilaterally disposed electrodes (FIG. 6A), and two contralaterally disposed electrodes (FIG. 6B)
Figure 6B:
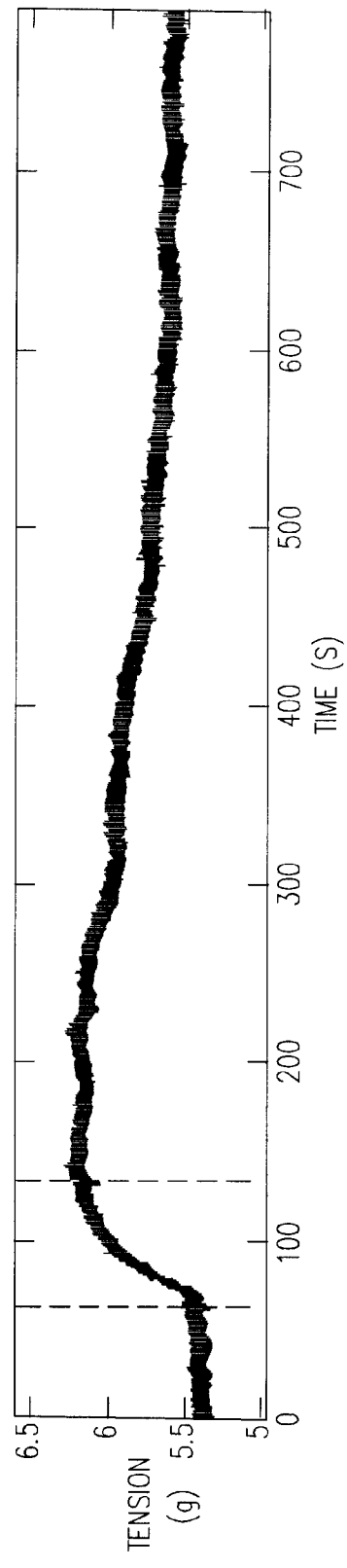

Reference is now made to FIGS. 6A-B, which are graphs showing the tension that was measured in aortic ring 80 before, during and after stimulation of the ring by, respectively, the two ipsilateral electrodes (FIG. 6A), and contralateral electrodes (FIG. 6B). The beginning and end of the stimulation periods are denoted by the vertical dashed lines in the graphs.

It may be observed that stimulation of the aortic ring with the ipsilateral electrodes (FIG. 6A) resulted in a decrease in the tension of the aortic ring. The aortic ring recovered its pre-stimulation level of tension about 150 seconds after the stimulation period finished. Stimulation of the aortic ring via contralateral electrodes (FIG. 6B) resulted in an increase in the tension of the ring. These results indicate that stimulating the aorta, and/or other arteries, using electrodes that are disposed ipsilaterally, and longitudinally with respect to one another causes a decrease in the tension in the arterial wall, i.e., the artery dilates. Stimulating the aorta, and/or other arteries, using electrodes that are disposed contralaterally to one another, with respect to the artery, causes an increase in the tension in the arterial wall, i.e., the artery contracts.

Thus, for some applications of the invention, an artery is constricted by driving a current into the artery via electrodes that are disposed contralaterally to each other, with respect to the artery. Alternatively or additionally, an artery is dilated by driving a current into the artery via electrodes that are disposed ipsilaterally to each other, with respect to the artery. For example, in order to dilate a coronary artery, in accordance with the techniques described hereinabove, current is driven into the heart via electrodes that are disposed ipsilaterally to each other, with respect to the coronary artery.

Figure 7A:
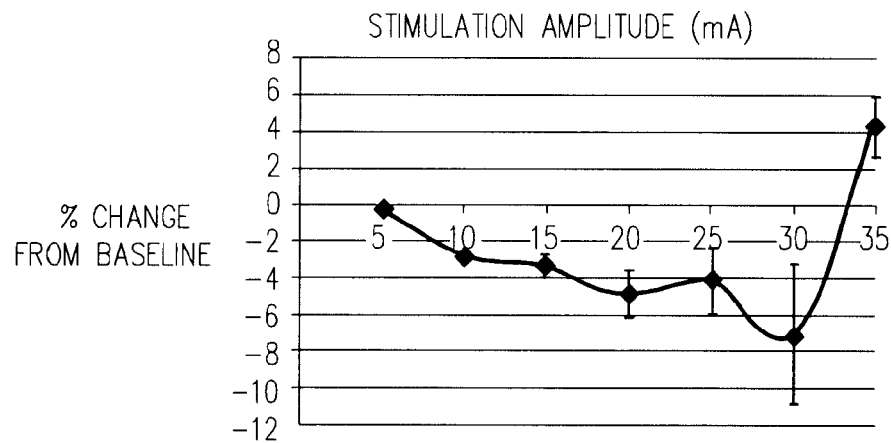
FIGS. 7A-C are graphs showing the tension that was measured in the aortic ring during stimulation of the ring with the ipsilaterally disposed electrodes using respective stimulation parameters.
Figure 7B:
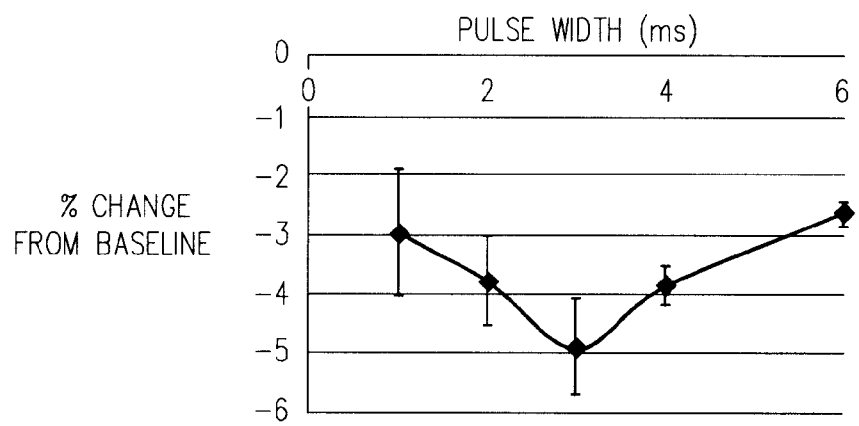
Figure 7C:
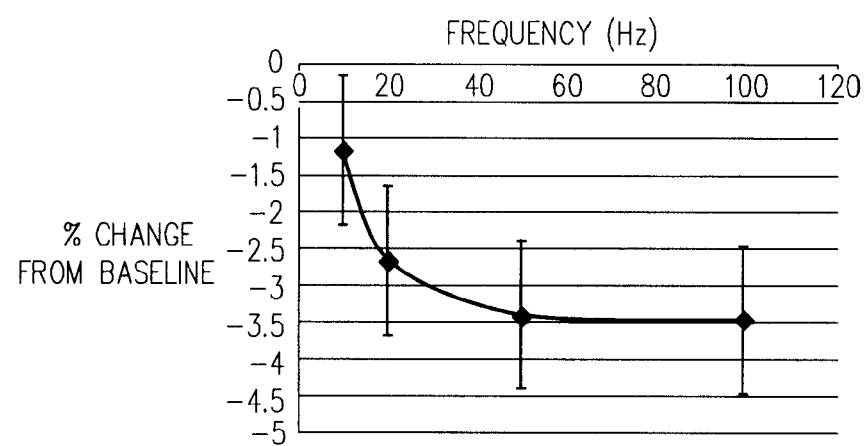

Reference is now made to FIGS. 7A-C, which are graphs showing the tension that was measured in aortic ring 80 during stimulation of the ring with ipsilateral electrodes 88, using respective stimulation parameters.

FIG. 7A is a graph showing the change in the tension measured in aortic ring 80 relative to the pre-stimulation tension in the ring, during stimulation of the ring with a current having a pulse width of 4 ms, and a frequency of 50 Hz, over a range of amplitudes. It may be observed that the greatest decrease in the tension in the ring was for currents having amplitudes of more than 15 mA, and/or less than 35 mA (e.g., 15 mA-35 mA), for example, more than 25 mA, and/or less than 33 mA (e.g., 25 mA-33 mA).

FIG. 7B is a graph showing the change in the tension measured in aortic ring 80 relative to the pre-stimulation tension in the ring, during stimulation of the ring with a current having an amplitude of 15 mA, and a frequency of 50 Hz, for a range of pulse widths. It may be observed that the greatest decrease in the tension in the ring was for currents having pulse widths of more than 1 ms, and/or less than 5 ms (e.g., 1 ms-5 ms), for example, more than 2 ms, and/or less than 4 ms (e.g., 2 ms-4 ms).

FIG. 7C is a graph showing the change in the tension measured in aortic ring 80 relative to the pre-stimulation tension in the ring, during stimulation of the ring with a current having a pulse width of 4 ms, and an amplitude of 15 mA, for a range of frequencies. It may be observed that the greatest decrease in the tension in the ring was for currents having a frequency of more than 20 Hz (e.g., more than 50 Hz), for example, 20 Hz-100 Hz.

Thus, for some applications, a subject is identified as suffering from a condition, which may be at least partially treated by causing the subject's coronary arteries to dilate, as described hereinabove. In response to the identification, electrodes are placed in contact with the subject's heart such that the electrodes are disposed ipsilaterally to each other, with respect to a coronary artery, in accordance with the results shown in FIG. 6A.

For some applications, a current having one or more of the following parameters is driven via the electrodes, in order to cause dilation of a coronary artery of the subject, in accordance with the results shown in FIGS. 7A-C:

an amplitude of more than 15 mA, and/or less than 35 mA (e.g., 15 mA-35 mA), for example, more than 25 mA, and/or less than 33 mA (e.g., 25 mA-33 mA);
  a pulse width of more than 1 ms, and/or less than 5 ms (e.g., 1 ms-5 ms), for example, more than 2 ms, and/or less than 4 ms (e.g., 2 ms-4 ms); and/or
  a frequency of more than 20 Hz (e.g., more than 50 Hz), for example, 20 Hz-100 Hz.

Figure 8C:
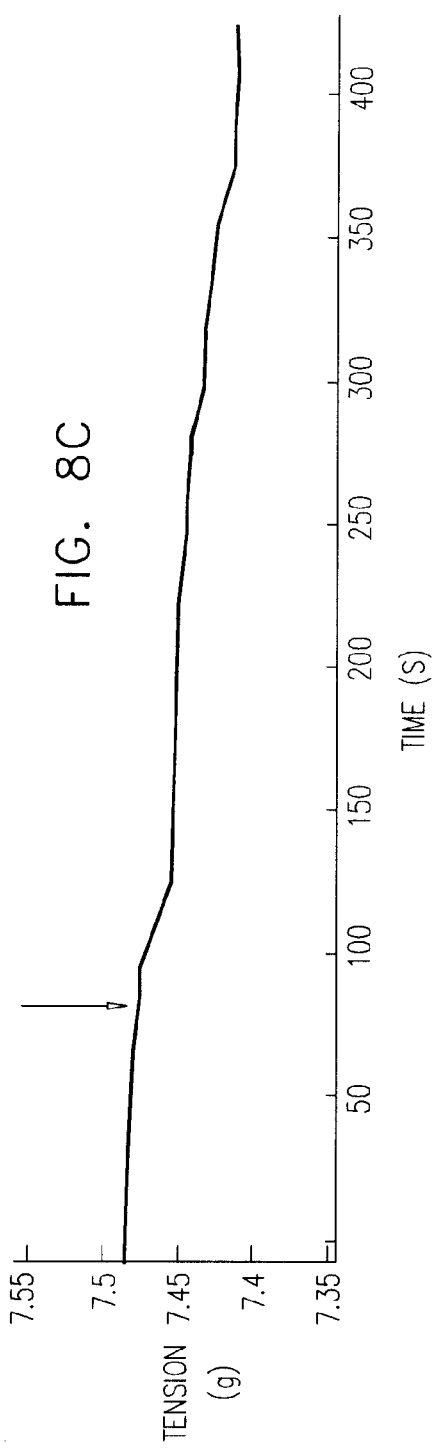
Figure 8D:
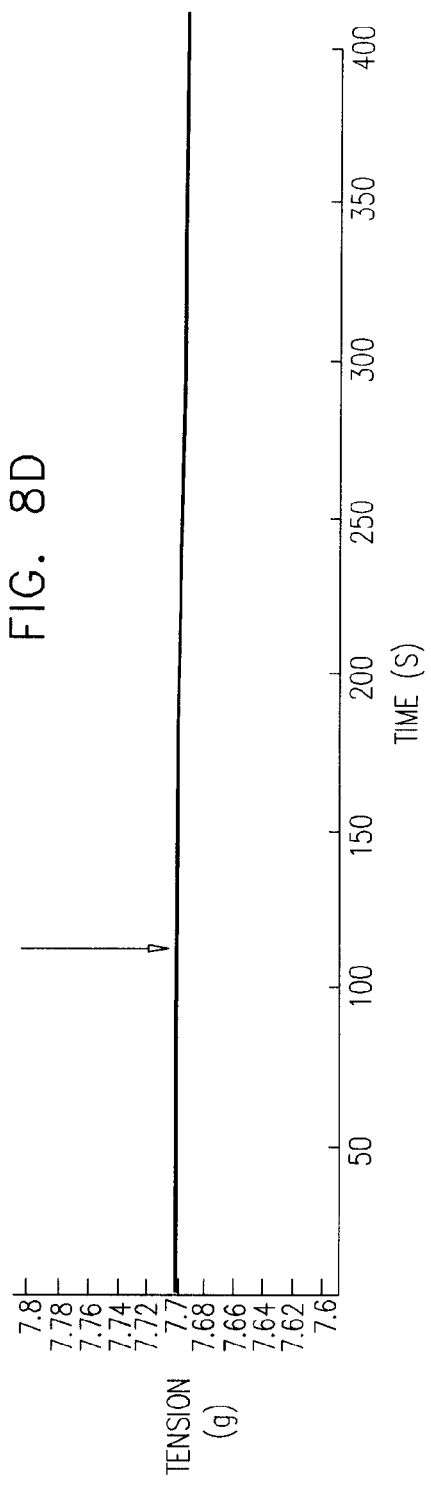

Reference is now made to FIGS. 8A-D, which are graphs showing the tension measured in aortic ring 80 in response to electrical stimulation (FIGS. 8A-B), and in response to the administration of substance P neuropeptide (FIGS. 8C-D).

FIG. 8A is a graph showing the tension measured in an aortic ring measured before, during, and after stimulation of the ring with ipsilateral electrodes using a current having an amplitude of 15 mA, a frequency of 50 Hz, and a pulse width of 4 ms. The beginning and end of the stimulation period is denoted by the vertical dashed lines on FIG. 8A.

FIG. 8B shows the tension measured in an aortic ring before, during, and after stimulation of the ring with ipsilateral electrodes using a current having an amplitude of 15 mA, a frequency of 50 Hz, and a pulse width of 4 ms. Before stimulating the aortic ring to collect the data shown in FIG. 8B, the endothelial wall of the aortic ring was mechanically denuded. The beginning and end of the stimulation period is denoted by the vertical dashed lines on FIG. 8B.

FIG. 8C is a graph showing the tension measured in an aortic ring measured before, and after administration of substance P neuropeptide to the aortic ring. The time at which the substance P was administered is denoted by the downward-pointing arrow in FIG. 8C.

FIG. 8D is a graph showing the tension measured in an aortic ring measured before, and after administration of substance P neuropeptide to the aortic ring. The time at which the substance P was administered is denoted by the downward-pointing arrow in FIG. 8D. Before stimulating the aortic ring and collecting the data shown in FIG. 8D, the endothelial wall of the aortic ring was mechanically denuded.

It may be observed that electrical stimulation of the aortic ring before the endothelial denuding, resulted in the aortic ring having reduced tension, as demonstrated by FIG. 8A. Subsequent to the endothelial denuding, electrical stimulation of the aortic ring did not cause a reduction in the tension in the aortic ring. Similarly, administration of substance P caused a reduction in the tension of the aortic ring before the endothelial denuding (as demonstrated by FIG. 8C), but did not cause a reduction in the tension of the aortic ring subsequent to the endothelial denuding (as demonstrated by FIG. 8D).

Substance P is a vasodilator. Substance-P-induced vasodilation has been shown to be dependent on the release of nitric oxide from the endothelium (c.f. "In vivo measurement of endothelium-dependent vasodilation with substance P in man," Bossaller, Herz. 1992 October; 17(5):284-90). This explains the data shown in FIGS. 8C-D, namely, that substance P was effective at reducing tension in the aortic ring before the endothelial denuding, but not subsequent to the endothelial denuding.

In view of the above, the data shown in FIGS. 8A-B, indicate that the mechanism by which electrical stimulation of the aortic ring causes the aortic ring to dilate is at least partially due to the release of endothelium-derived nitric oxide NO. Thus, subsequent to endothelial denuding, electrical stimulation is not effective to dilate the aortic ring.

Embodiments of the present invention may be practiced in combination with techniques described in one or more of the following references, which are incorporated herein by reference:

U.S. Pat. No. 5,800,464 to Kieval et al.
U.S. Pat. No. 6,141,587 to Mower et al.
U.S. Pat. No. 6,411,845 to Mower et al.
U.S. Pat. No. 7,062,318 to Ben-Haim et al.
U.S. Pat. No. 6,947,792 to Ben-Haim et al.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a heart of a subject, comprising:
   a set of one or more electrodes; and
   a control unit, configured to:
   pace the heart by driving a first electric current via the electrode set into tissue of the subject, in accordance with a first set of parameters, and
   stimulate nitric oxide production by a portion of the heart by driving a second electric current via the electrode set into the portion of the heart, in accordance with a second set of parameters.

2. The apparatus according to claim 1, further comprising a sensor configured to sense a level of activity of the subject and to generate a signal in response thereto, wherein the control unit is configured to:
   set a parameter of the first electric current in response to the signal, and
   designate a frequency parameter of the second electric current independently of the signal.

3. The apparatus according to claim 1, wherein the control unit is configured to stimulate the nitric oxide production substantially without causing action potentials in the portion of the heart.

4. The apparatus according to claim 1, wherein the control unit is configured to stimulate the nitric oxide production by the portion of the heart by driving the second electric current with a frequency of more than 20 Hz.

5. The apparatus according to claim 1, further comprising a detector configured to detect a cardiac cycle of the subject and to generate a signal in response thereto, wherein the control unit is configured to receive the signal and, in response thereto, to drive the second current in coordination with the cardiac cycle of the subject.

6. The apparatus according to claim 5, wherein the control unit is configured to detect an ECG signal of the subject and to initiate driving of the second current in response to detecting an R-wave of the subject's ECG signal.

7. The apparatus according to claim 1, wherein the control unit is configured to stimulate the nitric oxide production by the portion of the heart by configuring the second electric current to have an amplitude of 15-35 mA.

8. The apparatus according to claim 7, wherein the control unit is configured to stimulate the nitric oxide production by the portion of the heart by configuring the second electric current to have an amplitude of 25-33 mA.

9. The apparatus according to claim 1, wherein the control unit is configured to stimulate the nitric oxide production by driving the second current as a train of pulses into the portion of the heart.

10. The apparatus according to claim 9, wherein the control unit is configured to configure each pulse to have a pulse width of 1-5 ms.

11. A method for treating a heart of a subject, comprising:
    pacing the heart by driving a first electric current into tissue of the heart, in accordance with a first set of parameters; and
    stimulating nitric oxide production by a portion of the heart by driving a second electric current into the portion of the heart, in accordance with a second set of parameters.

12. The method according to claim 11, wherein stimulating the nitric oxide production comprises stimulating the nitric oxide production substantially without inducing action potentials in the portion of the heart.

13. The method according to claim 11, further comprising detecting a cardiac cycle of the subject, wherein stimulating the nitric oxide production comprises driving the second electric current in coordination with the detected cardiac cycle.

14. The method according to claim 13, wherein detecting the subject's cardiac cycle comprises detecting an ECG signal of the subject and wherein driving the second electric current comprises initiating driving of the second current in response to detecting an R-wave of the subject's ECG signal.

15. The method according to claim 11, wherein stimulating the nitric oxide production comprises driving the second electric current as a train of pulses into the portion of the heart of the subject.

16. The method according to claim 15, wherein driving the second current comprises driving the second current as a train of pulses, wherein each pulse is configured to have a pulse width of 1 ms to 5 ms.

17. The method according to claim 11, wherein driving the second electric current into the portion of the heart comprises driving the second electric current with an amplitude of 15-35 mA.

18. The method according to claim 17, wherein driving the second electric current into the portion of the heart comprises driving the second electric current with an amplitude between of 25-33 mA.

19. The method according to claim 18, wherein stimulating the nitric oxide production comprises driving the second electric current into the portion of the heart with a frequency between 20 Hz and 100 Hz.

20. Apparatus for use with a heart of a subject, comprising:
a set of one or more electrodes configured to be implanted into an outer surface of the heart;
a control unit, configured to stimulate nitric oxide production by a portion of the heart by driving the electrodes to drive an electric current into the outer surface of the heart; and
a mesh supporting the set of electrodes, and configured to be implanted around the outer surface of the heart.

21. The apparatus according to claim 20, wherein at least one of the electrodes comprises a screw electrode.

22. The apparatus according to claim 20, wherein the mesh is configured to inhibit remodeling of the heart by applying a compressive force to the heart.

23. The apparatus according to claim 20, wherein the mesh is configured to apply a force to the heart that is insufficient to inhibit remodeling of the heart.

* * * * *